United States Patent [19]
Kusunoki et al.

[11] Patent Number: 5,654,165
[45] Date of Patent: Aug. 5, 1997

[54] ANTIBACTERIAL DRUG INSPECTION METHOD AND APPARATUS THEREFOR

[75] Inventors: Shin-ichiro Kusunoki, Tokyo; Jun-ichiro Arai, Tsukuba, both of Japan

[73] Assignee: Daikin Industries, Ltd., Osaka, Japan

[21] Appl. No.: 476,103

[22] Filed: Jun. 7, 1995

Related U.S. Application Data

[63] Continuation of Ser. No. 211,163, filed as PCT/JP93/01017, Jul. 21, 1993, abandoned.

[30] Foreign Application Priority Data

Jul. 22, 1992 [JP] Japan .................... 4-195468

[51] Int. Cl.$^6$ ........................................ C12Q 1/20
[52] U.S. Cl. ............... 435/32; 435/33; 435/286.1; 435/286.4; 435/287.1; 435/287.3
[58] Field of Search ............. 435/32, 33, 286.1, 435/286.4, 287.1, 287.3

[56] References Cited

U.S. PATENT DOCUMENTS

| | | | |
|---|---|---|---|
| 4,246,343 | 1/1981 | Wilkins et al. | 435/32 |
| 4,288,543 | 9/1981 | Sielaff et al. | 435/34 |
| 4,861,709 | 8/1989 | Ulitzur et al. | 435/6 |

FOREIGN PATENT DOCUMENTS

| | | |
|---|---|---|
| 53-99379 | 8/1978 | Japan . |
| 56-140898 | 4/1981 | Japan . |
| 3-198767 | 8/1991 | Japan . |

*Primary Examiner*—Milton Cano
*Attorney, Agent, or Firm*—Beveridge, DeGrandi, Weilacher & Young, LLP

[57] ABSTRACT

A test solution including bacteria is added to a liquid sample in which antibacterial drug exists and to a liquid sample in which no antibacterial drug exists, and existence or non-existence of drug sensitivity is judged based upon whether or not the dissolved oxygen concentration in both liquid samples are essentially different from one another.

23 Claims, 7 Drawing Sheets

ANTIBACTERIAL DRUG INSPECTION METHOD AND APPARATUS THEREFOR

This is a continuation of Ser. No. 08/211,163 filed on Apr. 26, 1994 which represents the national stage filing of PCT/JP93/01017 filed Jul. 21, 1993, now abandoned.

1. Technical Field

This present invention relates to an antibacterial drug inspection method and apparatus therefor, and, more particularly, this present invention relates to a method and apparatus for inspecting whether or not bacteria, which is a cause of infectious disease and the like, has drug sensitivity to a specific antibacterial drug.

2. Background Art

When medical care for an infectious disease caused by bacteria is performed in clinical iatrology, there is often employed as a general medical care method a dosage of an antibacterial drug (antibiotic resistance, bactericidal drug and the like) to which the bacteria causing the infectious disease has drug sensitivity. But, it must be determined prior to dosing the antibacterial drug whether the bacteria causing the infectious disease has drug sensitivity to the antibacterial drug. It is known that following general usage of an antibiotic resistance, for example, for medical care of an infectious disease, bacteria having a resistance to the antibiotic resistance appears. Further, even when the most recent antibiotic drug is applied to bacteria which previously showed no resistance at all to the antibiotic drug resistant bacteria appears which has resistance to the most recent antibiotic drug.

The minimum inhibitory concentration (MIC) measuring method established by Nihon Kagaku Ryouhou Gakkai and a method using liquid medium have been proposed as drug sensitivity inspection methods for satisfying such demand.

The MIC measuring method is a method for inoculating bacteria in a concentration of $10^6$ articles/ml, for example, onto an agar medium which includes an antibacterial resistance or drug in a predetermined concentration. The bacteria is also inoculated into another medium sample of the same type, but without the antibacterial resistance or drug. The bacteria inoculated onto the agar medium in both samples is incubated for a predetermined time (about 18–20 hours), and the drug sensitivity of the corresponding bacteria is determined by visually judging whether or not colonies are generated. Consequently, it is possible to judge whether or not bacteria has drug sensitivity. It is also possible to determine the degree of drug sensitivity of the bacteria, by preparing plural agar medium samples with the antibacterial drug concentration of each agar medium being different.

The aforementioned "method using liquid medium" is a method which utilizes the process involved in the MIC method except a liquid medium is used instead of the agar medium. The liquid medium method judges whether or not the bacteria has drug sensitivity and degree of drug sensitivity of the bacteria based upon turbidity of the liquid medium, variation in pH and the like.

Because both of the above-mentioned methods are of the MIC type, there is required a pretreatment adjustment step involving the separation of bacteria shares which requires an extremely long time to perform. Also, after the adjustment, the above-mentioned predetermined time for incubation is required. Thereby, a disadvantage arises in that the required time for carrying out an MIC type method in its entirety becomes extremely long. Specifically, the required time is 18–20 hours after adjustment for separation of the bacteria share when the MIC method is employed, and the required time ranges from several hours to 20 hours after adjustment for separation of the bacteria share when the method using liquid medium is employed. This long processing time is problematic especially in view of the strong demand to shorten the above-mentioned required time in order to provide for early treatment while still taking into consideration the requirement of determining drug sensitivity accurately.

Since the MIC measuring method visually judges the generated colonies, it may be thought that it is possible to completely automate the MIC measuring method by using a CCD camera or the like, for example. However, the type of bacteria that is subjected to a drug sensitivity inspection for treatment of an infectious disease and the like is not always known. Also, the manner of multiplication of bacteria greatly differs depending upon the type of bacteria. Therefore, it is almost impossible to achieve with a CCD camera the sensitivity adjustment required for adapting to various types of bacteria especially when the type is not known. In view of the complexities involved, there is lacking an apparatus which automatically performs a drug sensitivity inspection of an antibacterial drug applied to a bacteria whose type is not known.

DISCLOSURE OF THE INVENTION

This present invention was made to solve the above-mentioned problems.

It is an object of the present invention to supply a novel antibacterial drug inspection method and apparatus therefor. The novel method and apparatus of the present invention includes inspecting within a short time frame the drug sensitivity of a bacteria in a liquid subjected to an antibacterial drug and automating a series of inspection steps.

To achieve the above-mentioned object, an antibacterial drug inspection method for inspecting existing antibacterial drug in a liquid in which bacteria exists is provided. The method includes detecting the dissolved oxygen quantity in the liquid, judging whether or not the dissolved oxygen quantity essentially varies in the condition that the antibacterial drug exists in the liquid with respect to a dissolved oxygen quantity in a liquid in which the antibacterial drug does not exist, and judging whether the bacteria has drug sensitivity to the corresponding antibacterial drug only when the dissolved oxygen quantity varies. The term "antibacterial drug" is used in the present invention to include an antibiotic resistance, a bactericidal drug and the like. As to adding order to the step of combining the antibacterial drug and the bacteria in the liquid, one of the antibacterial drug and bacteria may be added prior to another, or both may be added simultaneously. Further, the concentration of antibacterial drug to be added is preferably placed at a higher concentration (for example, about 10–100 times the usual concentration) than the usual concentration used in the art.

An antibacterial drug inspection method according to the present invention is also a method for additionally including a respiration interfering drug and/or bacteria non-sensitive respiration interfering drug in the liquid in which the bacteria exists. Rotenone, amytal, antimycin A, cyanogen compound and the like are examples of respiration interfering drugs that can be used, and oligomycin, atractyloside and the like are examples of bacteria non-sensitive respiration interfering drugs that can be used, while body fluid, urine, lixiviation fluid, tissue fluid, tissue wash liquid, culture solution and the like are examples of the liquid in which the bacteria can be placed.

The present invention also features an antibacterial drug inspection apparatus which includes at least two culture cell means, test solution injection means for supplying a liquid in which bacteria exists to each culture cell means, oxygen electrode means each corresponding to each culture cell means, and judging means for judging whether or not an output signal from an oxygen electrode means corresponding to one culture cell means is essentially different from an output signal from an oxygen electrode means corresponding to the other culture cell means, and wherein an antibacterial drug is present in only one of the culture cell means such that other culture cell means is free of the antibacterial drug. The term "antibacterial drug" includes, for example, an antibiotic resistance, a bactericidal drug and the like. To provide greater order in the placement of the antibacterial drug and the bacteria in the liquid, one of the antibacterial drug and bacteria may be added prior to the other, or both may be added simultaneously. Further, the concentration of the antibacterial drug to be added is preferably placed at a significantly higher concentration (for example, about 10–100 times to the usual concentration) than the usual concentration relied upon in the art.

The antibacterial drug inspection apparatus of the present invention additionally provides a respiration interfering drug and/or a bacteria non-sensitive respiration interfering drug in each culture cell means. Rotenone, amytal, antimycin A, cyanogen compound and the like are examples of an applicable respiration interfering drug, and oligomycin, atorakuchirosido and the like are examples of bacteria non-sensitive respiration interfering drugs.

In accordance with the antibacterial drug inspection method of the present invention, when the bacteria in the liquid has a drug sensitivity to the corresponding antibacterial drug, the consumption quantity of the dissolved oxygen in the liquid decreases due to the decrease in the living number of bacteria. On the contrary, when the bacteria in the liquid has no drug sensitivity to the corresponding antibacterial drug, or when no antibacterial drug is present in the liquid, the consumption quantity of the dissolved oxygen in the liquid increases following. passage of time due to a multiplication of bacteria in the liquid. Therefore, it is possible to determine whether or not the bacteria in the liquid has drug sensitivity to the corresponding antibacterial drug by judging whether or not the dissolved oxygen quantities are essentially different between the case where the antibacterial drug exists in the liquid and in the case where no antibacterial drug exists in the liquid. Further, as is apparent from the above description, it is sufficient that the dissolved oxygen quantity is measured as soon as sufficient variations in the respiration amount of the bacteria appear. Thus, the required time after adjustment for separation of the bacteria share is extremely shortened.

As to the antibacterial drug inspection method of the present invention, because the respiration interfering drug and/or the bacteria non-sensitive respiration interfering drug is provided in the liquid in which the bacteria exists, the influence of respiration of animal cells other than the bacteria is eliminated, and the judgement accuracy of the drug sensitivity is improved. When the respiration interfering drug is placed in the liquid, it may be thought that respiration of both the bacteria and the animal cells other than the bacteria is interfered. But, as a result of research by the inventors when the respiration interfering drug is used in a usual concentration (for example, about 10–100 μM), a sufficient respiration interfering function to the animal cells is recognized, while scarce respiration interfering function to the bacteria is recognized. Therefore, when the respiration interfering drug is used in addition to or instead of the bacteria non-sensitive respiration interfering drug, influence of respiration of only the animal cells is securely eliminated, and the judging accuracy of drug sensitivity is improved.

In the antibacterial drug inspection apparatus of the present invention, the antibacterial drug is supplied to culture cell means except for at least one of the culture cell means, in this condition liquid in which bacteria exists is supplied to each culture cell means by the test solution injection means. Dissolved oxygen quantities in the culture cell means are measured by the oxygen electrode means, each oxygen electrode means corresponding to each culture cell means. And, it is judged by the judgement means whether or not the output signal from the oxygen electrode means corresponding to the one culture cell means without the antibacterial drug and the output from the oxygen electrode means corresponding to other culture cell means are essentially different from one another. When both output signals are not essentially different, it is judged that the bacteria has no drug sensitivity to the antibacterial drug, on the contrary, when both output signals are essentially different, it is judged that the bacteria has drug sensitivity to the antibacterial drug. Further, as is apparent from the above description, since judgment is based on the measurement of the dissolved oxygen quantity which varies in accordance with the respiration activity of the bacteria and since respiration begins right away, the required time after adjustment for the separation of the bacteria shares is extremely shortened. Furthermore, since the method involves measuring with an oxygen quantity detection device the dissolved oxygen quantities corresponding to the presence and non-presence of the antibacterial drug, and since judgment is based on whether or not both measurement signals are different from one another, the drug sensitivity of the bacteria is easily and accurately judged even when the type of the bacteria is not known. Therefore, the antibacterial drug inspection apparatus can easily be automated in its entirety with the assistance of control means.

As to the antibacterial inspection apparatus of the present invention, because a respiration interfering drug and/or a bacteria non-sensitive respiration interfering drug is/are placed in all culture cell means, the influence of the respiration of animal cells other than the bacteria is eliminated, and the judgement accuracy of drug sensitivity is improved.

BEST MODE FOR UTILIZING THE INVENTION

Referring to the attached drawings, we explain the present invention in detail.

Figure 1:
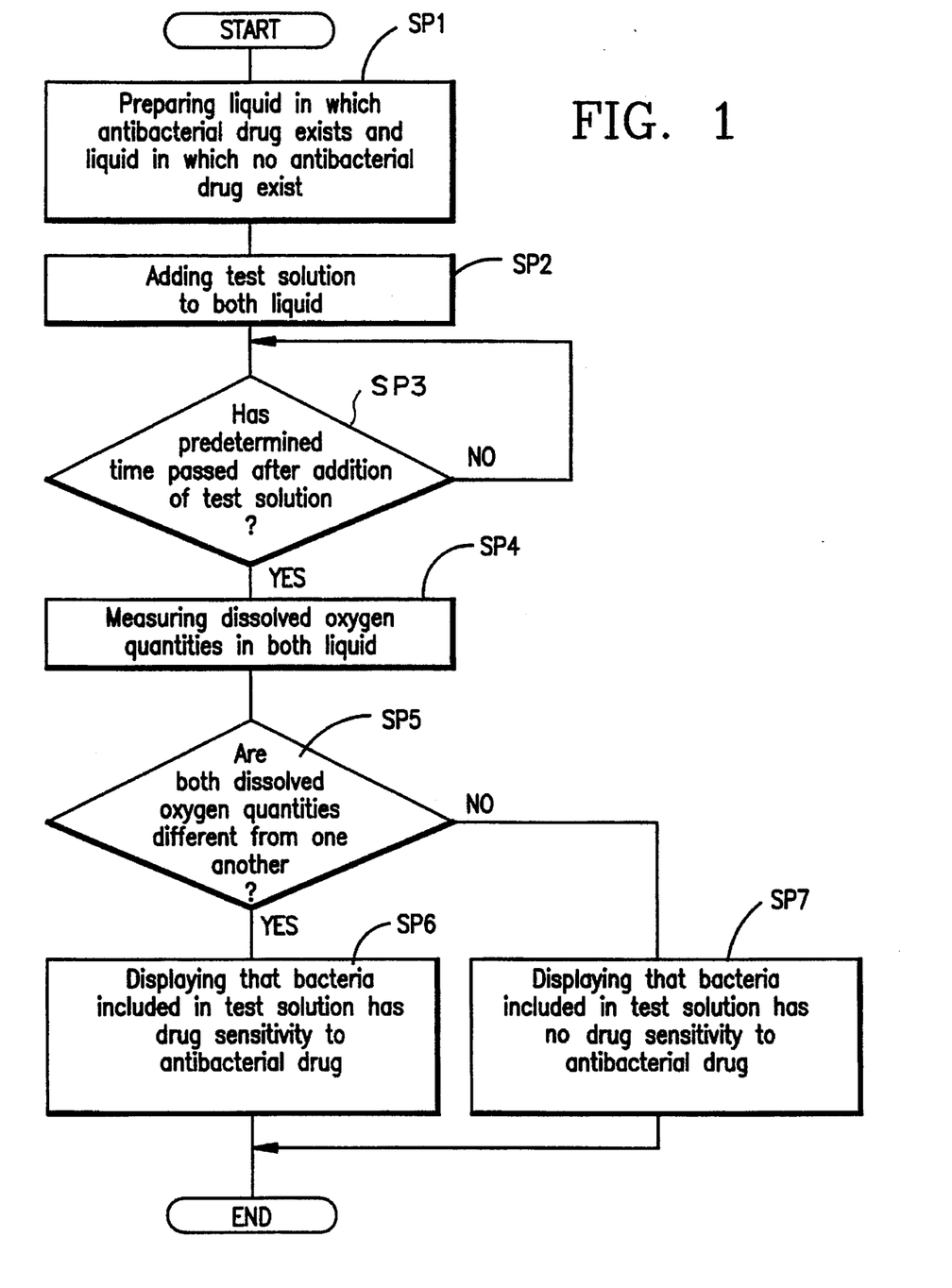
FIG. 1 is a flowchart for explaining an inspection sequence of an embodiment of an antibacterial drug inspection method according to the present invention.

FIG. 1 is a flowchart for explaining an inspection sequence of an embodiment of an antibacterial drug inspection method according to the present invention.

In step SP1, a liquid sample in which an antibacterial drug in a predetermined concentration (extremely higher concentration than a typical concentration used in the prior art) exists and a liquid sample in which no antibacterial drug exists are prepared. In step SP2, a test solution is added to both liquid samples. In step SP3, a determination is made as to whether or not there has passed a predetermined time period after the addition of the test solution to the culture cell means. In step SP4, the dissolved oxygen quantities in both liquid samples are measured. In step SP5, it is judged whether or not the measured dissolved oxygen quantities are essentially different from one another. When both dissolved oxygen quantities are essentially different from one another, step SP6 is carried out such that it is displayed that the bacteria included in the test solution has drug sensitivity to the antibacterial drug. On the contrary, when it is judged in step SP5 that both dissolved oxygen quantities are essentially equal to one another, step SP7 is carried out such that it is displayed that the bacteria included in the test solution has no drug sensitivity to the antibacterial drug.

In the above-mentioned step SP5, it is also judged whether or not both of the dissolved oxygen quantities are essentially different from one another, for the sake of eliminating the influence of error of the measurement system and the like.

In this embodiment, judgement whether or not bacteria has drug sensitivity is performed by waiting until the dissolved oxygen quantities can be judged to be essentially different from one another, a drug sensitivity inspection result can be obtained within 60 minutes at the longest after addition of the test solution.

Further, in the above described embodiment, a drug sensitivity test is conducted for one species of antibacterial drug. The method of the present invention also contemplates inspecting for more than one type of antibacterial drug in one process sequence. When drug sensitivity is inspected for two or more species of antibacterial drug, it is sufficient that plural liquid samples are prepared, with the different antibacterial drugs provided in separate liquid samples, and that dissolved oxygen quantities of the liquid samples in which an antibacterial drug exists and of the liquid in which no antibacterial drug exists is measured. It is then judged whether or not the former dissolved oxygen quantity and the latter dissolved oxygen quantity are essentially different from one another. For example, as the judgement sequence, the comparing of dissolved oxygen quantities may sequentially be performed for every liquid sample in which no antibacterial drug exists, or comparing the dissolved oxygen quantities may simultaneously be performed for all liquid samples in which no antibacterial drug exists. In both judging sequences, drug sensitivity to more than two species of antibacterial drug can be inspected almost simultaneously. Of course, it is possible that the liquid samples in which the antibacterial drug exists and the liquid samples in which no antibacterial drug exists are prepared as corresponding pairs.

Second Embodiment

Figure 2:
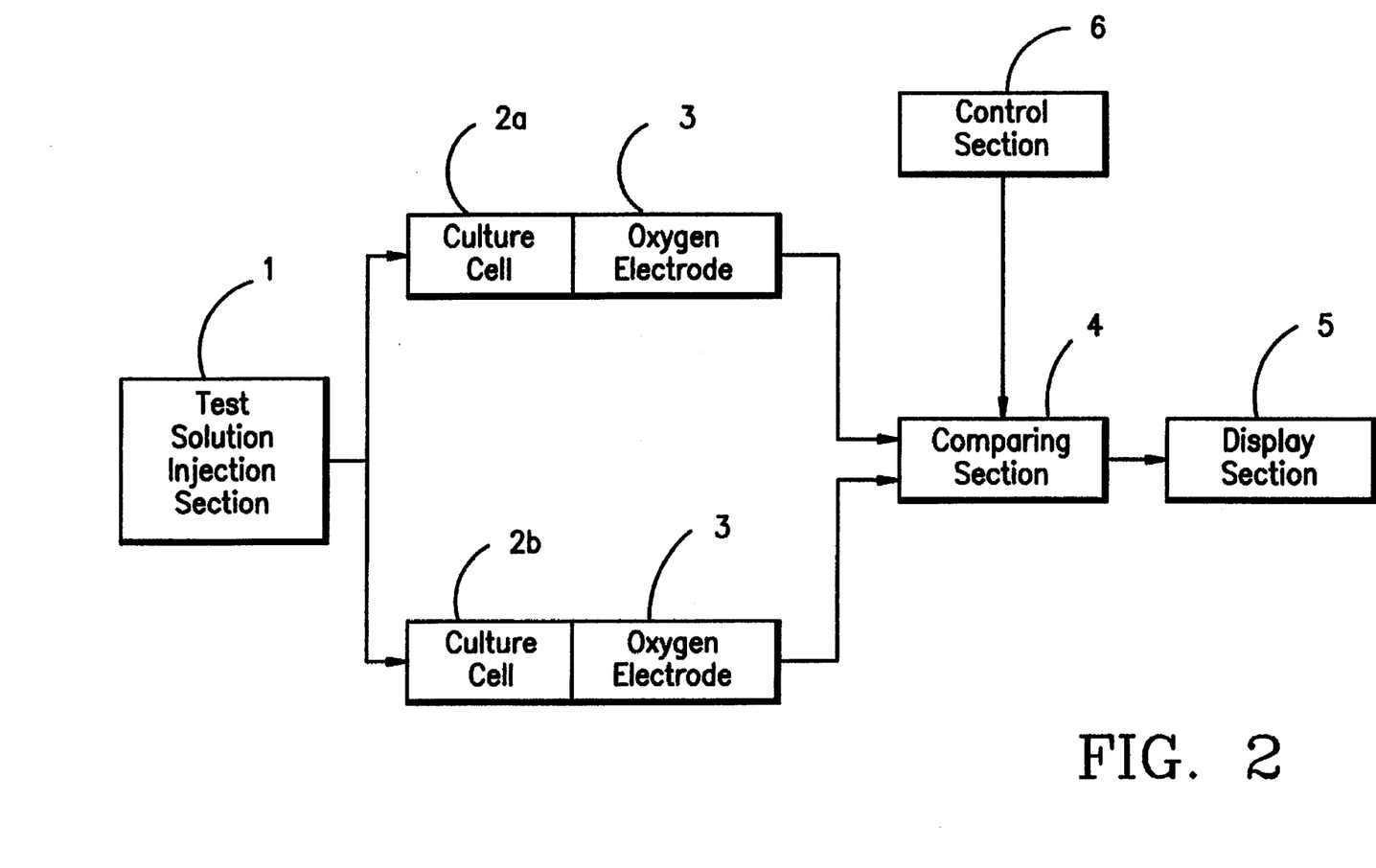
FIG. 2 is a schematic view illustrating an embodiment of an antibacterial drug inspection apparatus of the present invention.

FIG. 2 is a schematic view illustrating an embodiment of an antibacterial drug inspection apparatus of the present invention.

The antibacterial drug inspection apparatus includes two culture cells $2a$ and $2b$, a test solution injection section 1 for adding test solution to the culture cells $2a$ and $2b$ simultaneously, oxygen electrodes 3, each oxygen electrode being provided corresponding to each of both culture cells $2a$ and $2b$, a comparing section 4 for comparing output signals from both oxygen electrodes 3, and a display section 5 for displaying the existence or not of drug sensitivity in response to a comparison result of the comparing section 4. An antibacterial drug exists in only the one culture cell $2a$. The comparing section 4 judges that both output signals are different from one another only when a difference between both output signals is greater than a predetermined threshold value. Further, the antibacterial drug inspection apparatus includes a control section 6 for operating the comparing section 4 only after a predetermined time has passed since the addition of the test solution.

As to the antibacterial drug inspection apparatus having the above-mentioned arrangement, the culture cell $2a$ in which the antibacterial drug is provided and the culture cell $2b$ in which no antibacterial drug is provided are prepared, and in this condition, the test solution including bacteria is added to both culture cells $2a$ and $2b$ from the test solution injection section 1 simultaneously. Existence or non-existence of drug sensitivity of the bacteria is inspected as follows.

When the test solution is added, the antibacterial drug existing in the culture cell $2a$ comes in contact with the bacteria in the test solution. When the bacteria has drug sensitivity, the living number of bacteria decreases following passage of time due to the effect of the antibacterial drug. On the contrary, when the bacteria has no drug sensitivity and when the test solution is added to the culture cell in which no antibacterial drug exists, the living number of the bacteria increases following passage of time. Thereby, the consumption quantity of dissolved oxygen becomes small when the living number of bacteria decreases, while consumption quantity of dissolved oxygen becomes great when the living number of bacteria increases. Consequently, it is judged whether or not both output signals are essentially different from one another, that is whether or not drug sensitivity exists, by measuring dissolved oxygen quantities in each culture cell with the oxygen electrodes 3 at or after the predetermined time period has passed since the addition of the test solution, and by supplying the output signals from the oxygen electrodes 3 to the comparing section 4. Thereafter, existence or non-existence of drug sensitivity is displayed by the display section 5 in correspondence to the comparison result of the comparing section 4.

Further, in this embodiment, drug sensitivity is inspected as to one species of antibacterial drug. When drug sensitivity is inspected for two or more species of antibacterial drug, it is sufficient that plural liquid samples are prepared, with each antibacterial drug provided in a respective liquid sample, and that dissolved oxygen quantities of the liquid in which an antibacterial drug exists and of the liquid in which no antibacterial drug exists are determined, and that it is judged whether or not the former dissolved oxygen quantity and the latter dissolved oxygen quantity are essentially different from one another. For example, as the judgement sequence, comparing the dissolved oxygen quantities may sequentially be performed for every liquid sample in which no antibacterial drug exists, or comparing the dissolved oxygen quantities may simultaneously be performed for all of the liquid samples in which no antibacterial drug exists. In both judging sequences, drug sensitivity to two or more species of antibacterial drug can be inspected almost simultaneously. Of course, it is possible that the liquid sample in which the antibacterial drug exists and the liquid sample in which no antibacterial drug exist are prepared as pairs.

Third Embodiment

Figure 3:
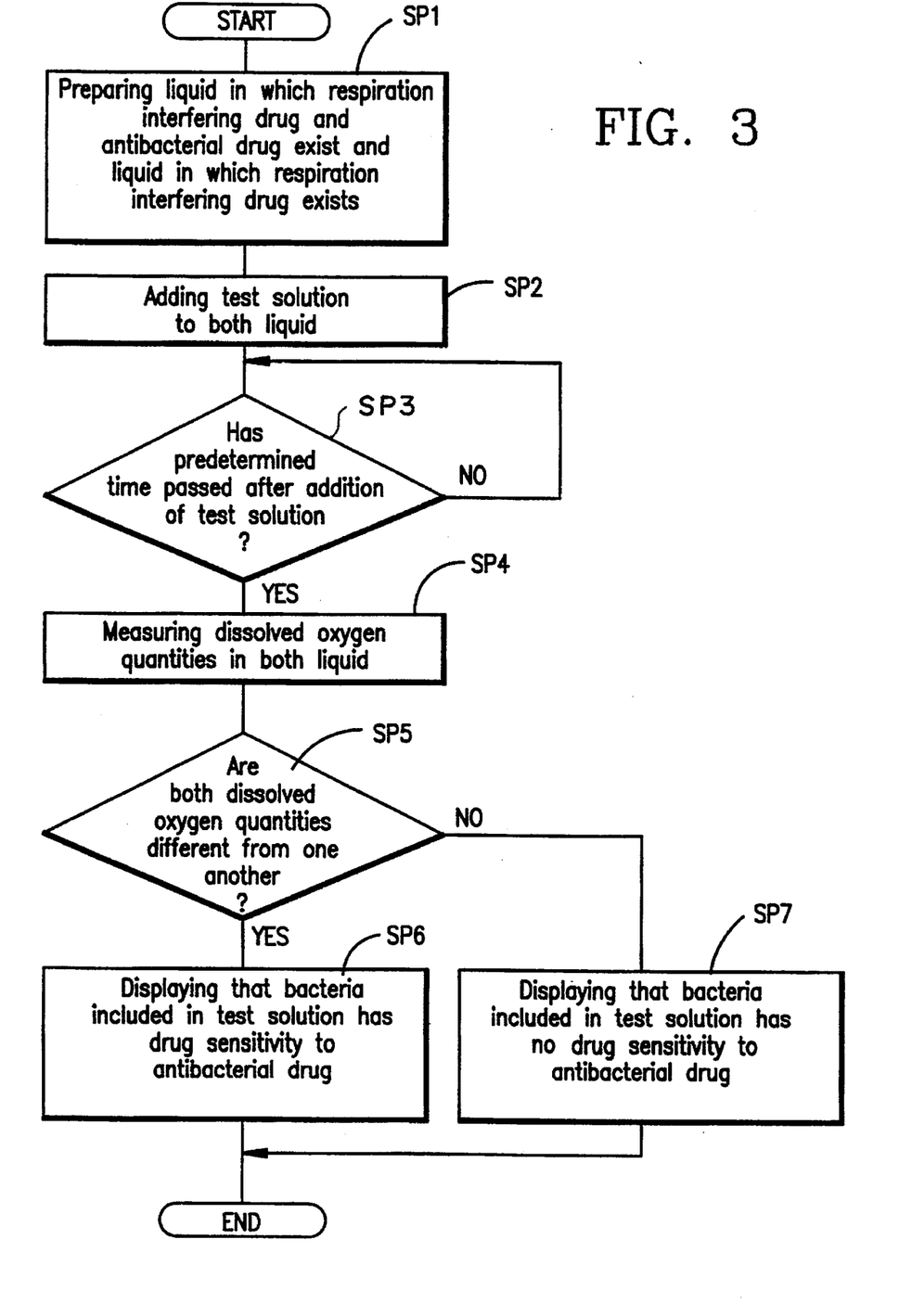
FIG. 3 is a flowchart for explaining an inspection sequence of another embodiment of an antibacterial drug inspection method according to the present invention.

FIG. 3 is a flowchart for explaining the inspection sequence of another embodiment of an antibacterial drug inspection method according to the present invention.

The flowchart differs from the flowchart in FIG. 1 only in that respiration interfering drug or bacteria non-sensitive respiration interfering drug is added to both liquid samples which are prepared in step SP1.

Therefore, in this embodiment, only the consumption quantity of dissolved oxygen (specifically, dissolved oxygen quantity at corresponding timing) caused by the living number of bacteria is measured by interfering with the respiration of animal cells other than bacteria in the test solution. Consequently, the influence of consumption of oxygen by animal cells is eliminated, and existence or non-existence of drug sensitivity is judged with high accuracy.

Fourth Embodiment

Figure 4:
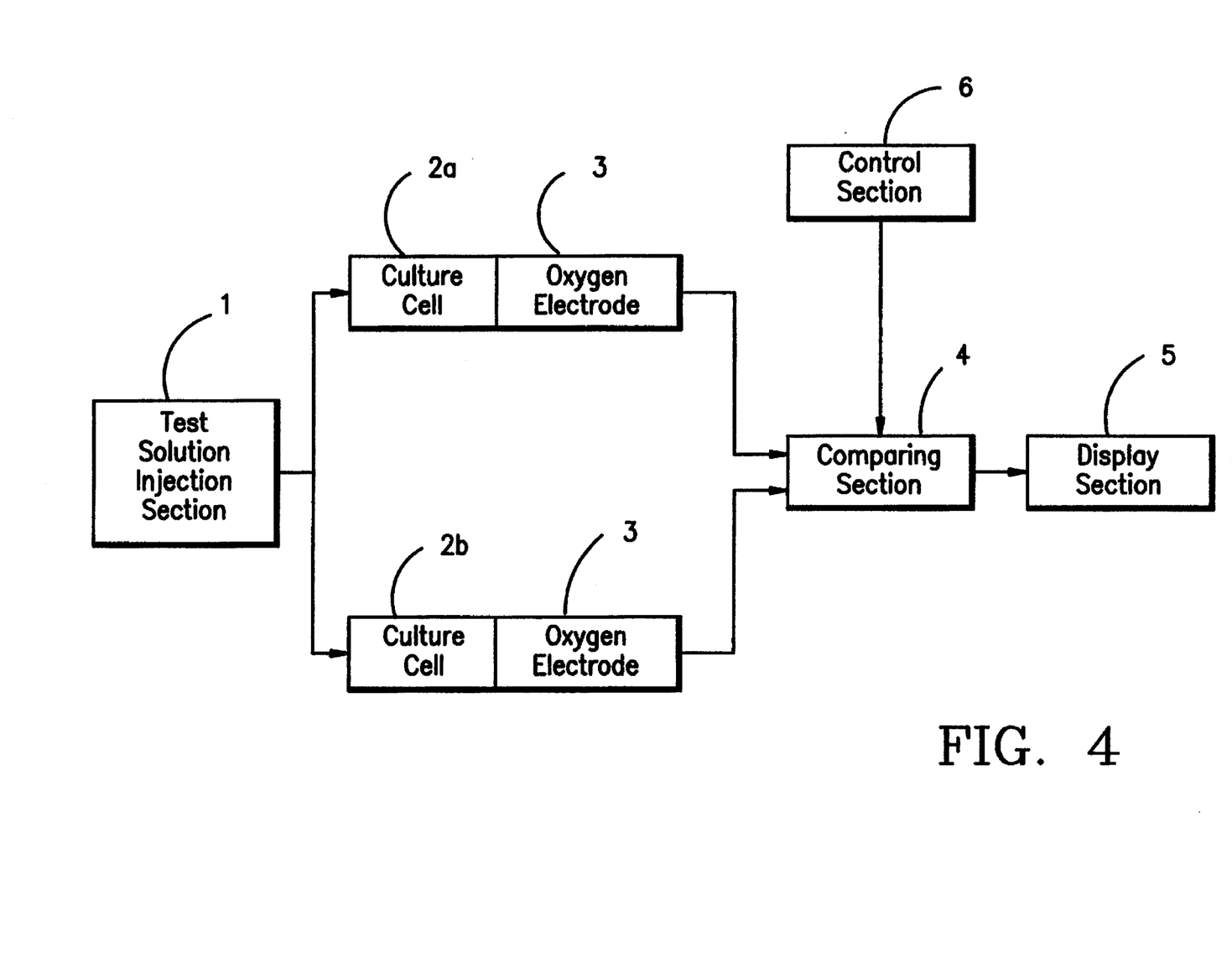
FIG. 4 is a schematic view illustrating another embodiment of an antibacterial drug inspection apparatus of the present invention.

FIG. 4 is a schematic view illustrating another embodiment of an antibacterial drug inspection apparatus of the present invention.

The apparatus differs from the embodiment in FIG. 2 only in that culture cells $2c$ and $2d$, in which a respiration interfering drug or a bacteria non-sensitive respiration interfering drug is added, are used instead of the culture cells $2a$ and $2b$.

Therefore, in this embodiment, only the consumption quantity of dissolved oxygen specifically, dissolved oxygen quantity at corresponding timing) caused by the living number of bacteria is measured by interfering with the respiration of animal cells other than bacteria in the test solution. Consequently, influence of consumption of oxygen by animal cells is eliminated, and existence or non-existence of drug sensitivity is judged with high accuracy.

SPECIFIC EXAMPLE

Figure 5:
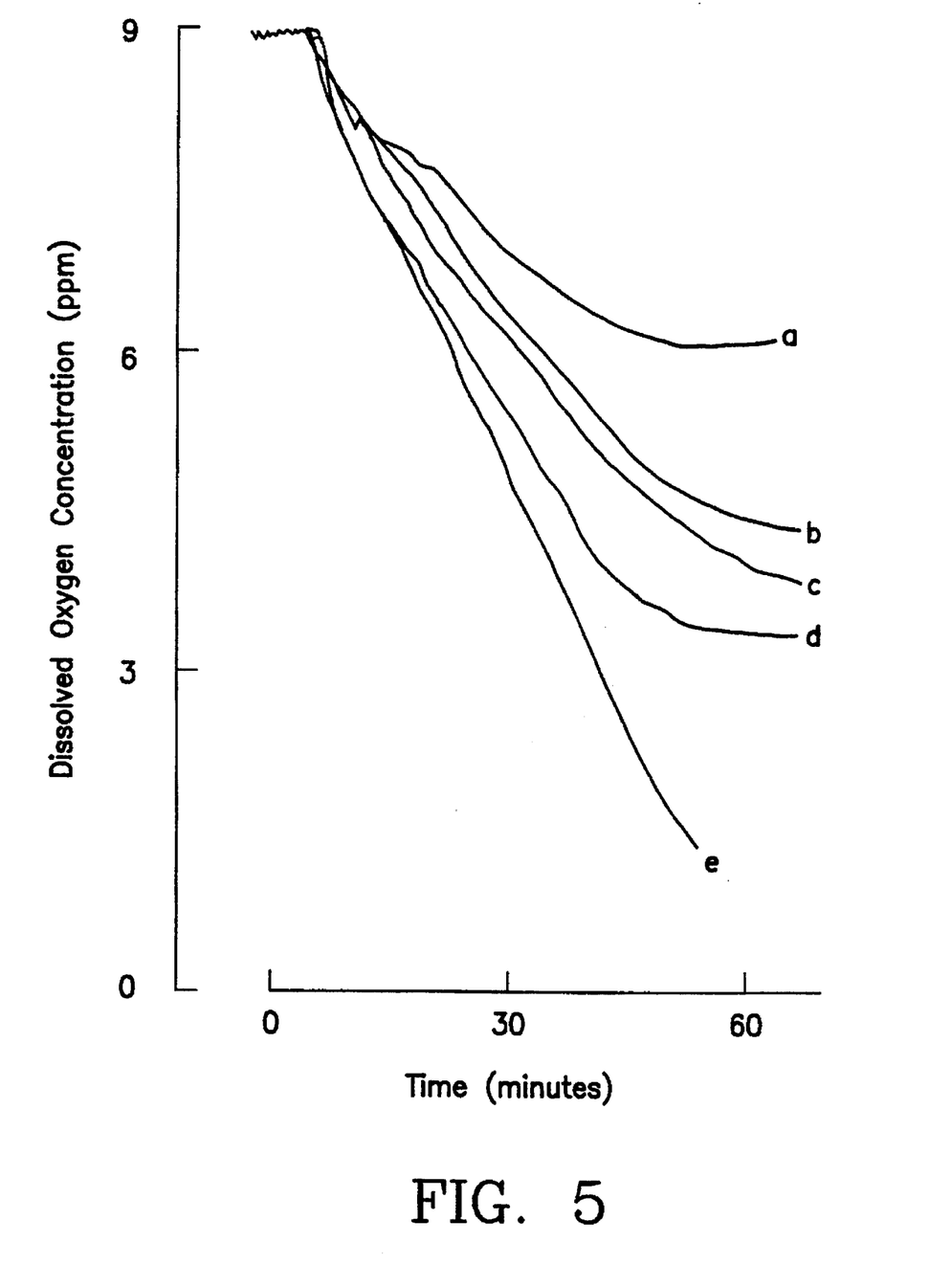
FIG. 5 is a diagram illustrating the variation of dissolved oxygen concentration following passage of time in a case wherein *E. coli* C#2021 is used as the bacteria.

FIG. 5 is a diagram illustrating the variation of dissolved oxygen concentrations in a case where $E.$ $coli$ C#2021 ($5 \times 10^6$ articles/ml) is used as the bacteria, and that ampicillin (added 500 g/ml), streptomycin (added 200μg/ml), chloramphenicol (added 200μ/ml) and tetracycline (added 40μg/ml) are used as the antibiotic resistance. In FIG. 5, a indicates ampicillin addition, b indicates streptomycin addition, c indicates chloramphenicol addition, d indicates tetracycline addition, and e indicates no antibiotic resistance addition.

As is apparent from FIG. 5, it is understood that the dissolved oxygen concentration almost linearly decreases following passage of the time when no antibiotic resistance is added, and that the dissolved oxygen concentration almost linearly decreases within some extent of time, and thereafter the decrease of the dissolved oxygen concentration is scarcely recognized, when antibiotic resistance is added. Further, linearly decreasing rates of a–d are smaller than the decreasing rate of e. Therefore, a–d and e are classified when 20–40 minutes has passed after addition of the test solution. That is, the existence or non-existence of drug sensitivity is judged accurately within a short time.

Figure 6:
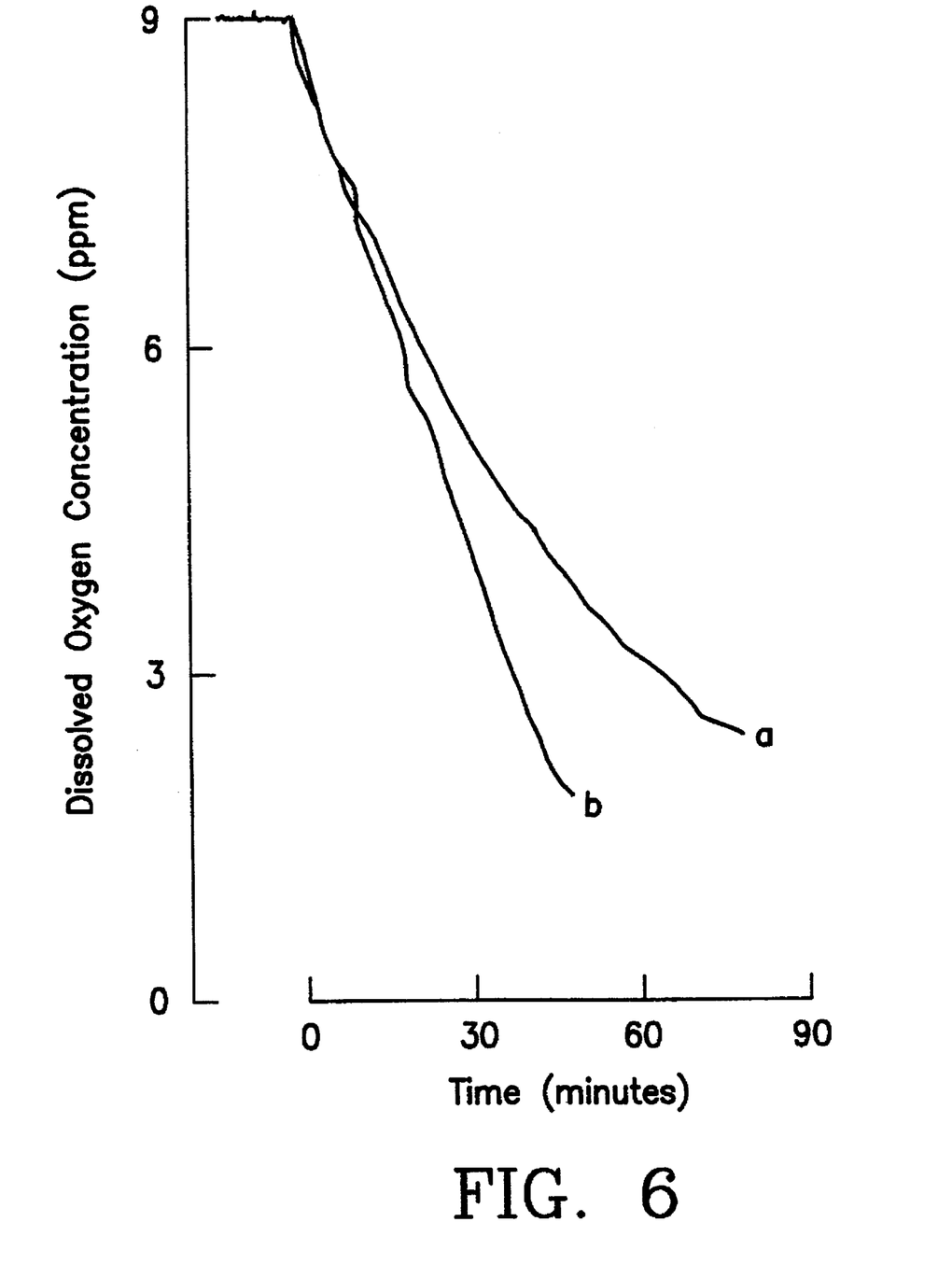
FIG. 6 is a diagram illustrating the variation of dissolved oxygen concentration following passage of the time in a case wherein *staphylococcus aureus* is used as the bacteria.

FIG. 6 is a diagram illustrating the variation of dissolved oxygen concentration in case that $staphylococcus$ $aureus$ ($S.$ $aureus$) ($1 \times 10^7$ articles/ml) is used as the bacteria, and that ampicillin (added 1 mg/ml) is used as the antibiotic resistance. In FIG. 6, a indicates ampicillin addition, b indicates no antibiotic resistance addition.

As is apparent from FIG. 6, both can securely be classified when about 40 minutes has passed. Further, a dissolved oxygen concentration variation characteristic similar to that shown in FIG. 6 is obtained when $K.$ $pneumoniae$ and $P.$ $aeruginosa$ are used.

Figure 7:
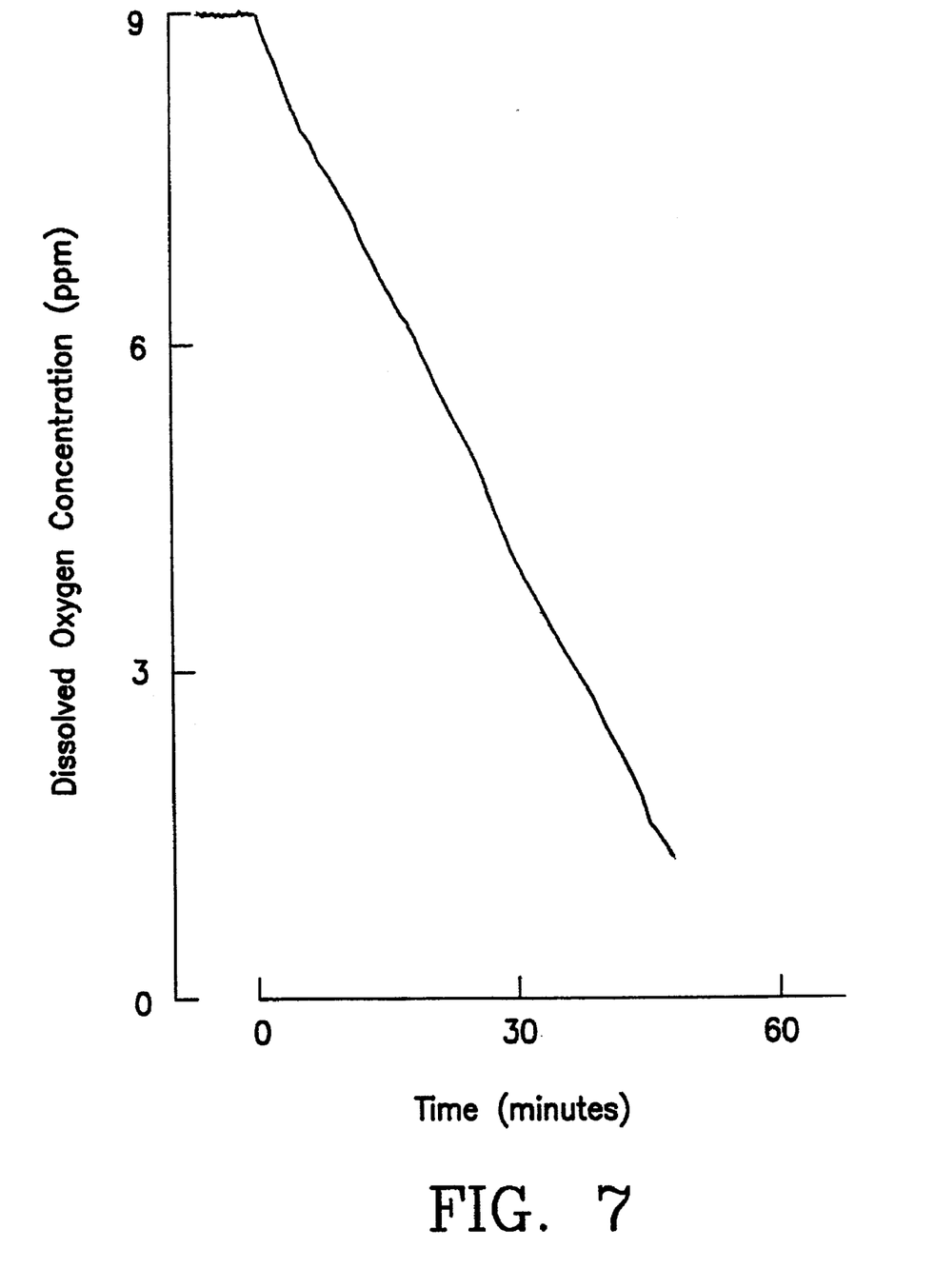
FIG. 7 is a diagram illustrating the variation of dissolved oxygen concentration following passage of time in a case wherein *E. coli* C#1181 is used as bacteria.

FIG. 7 is a diagram illustrating the variation of dissolved oxygen concentration in a case that $E.$ $coli$ C#1181 ($5 \times 10^6$ articles/ml) is used as the bacteria, and that streptomycin (added 200 μg/ml) is used as the antibiotic resistance.

As is apparent from FIG. 7, $E.$ $coli$ C#1181 indicates a reaction similar to e in FIG. 5. It is therefore understood that this bacteria is not influenced in spite of the addition of streptomycin. Thereby, non-existence of drug sensitivity is judged in this case.

Further, in the foregoing, description was made to a case wherein antibiotic resistance is used as the antibacterial drug, the inventors recognized that the respiration of $E.$ $coli$ ($1 \times 10$ articles/ml) is interfered with by using sulfanilamide (1 mg/ml). Therefore, bacteria is killed by interfering with the respiration. Also, an imidazole derivative drug and the like (other than sulfanilamide) can be used as an antibacterial drug, because an imidazole derivative drug and the like stops consumption of oxygen by bacteria.

The present invention is not limited to the embodiments mentioned above. The present invention may add antibacterial drug after the addition of the test solution. The present invention may also add the test solution and the antibacterial drug simultaneously. Further, various changes and modifications may be preferably made without departing from the spirit and scope of the invention.

POSSIBILITY OF INDUSTRIAL UTILIZATION

The present invention accurately judges within a short time whether or not the working of a micro-organism in a living body system, a reaction system and the like is suppressed by a drug. Therefore, the present invention is applicable to preprocessing (inspection) of medical care.

What is claimed is:

1. An antibacterial drug inspection method, comprising:
   detecting a dissolved oxygen quantity in at least a first and a second sample, with said first and second samples having a same type liquid medium and a same type bacteria, and with aid first sample including an antibacterial drug and said second sample being free of said antibacterial drug, and wherein said first and second samples include a respiration interfering drug, and wherein said detecting step includes positioning a first oxygen electrode device for sensing oxygen concentration such that said first oxygen electrode device comes in contact with said first test sample outputting a sensed value for said first test sample, and wherein said detecting step further includes positioning a second oxygen electrode device for sensing oxygen concentration such that said second oxygen electrode device comes in contact with said second test sample outputting a sensed value for said second test sample;
   comparing the outputted sensed values of said first and second oxygen electrode devices and outputting a comparison result; and
   determining whether the bacteria has a drug sensitivity to said antibacterial drug based on the outputted comparison result.

2. A method as recited in claim 1 wherein determining whether the bacteria has a drug sensitivity includes determining that the bacteria has a drug sensitivity when the dissolved oxygen quantity in said samples are different from each other by at least a reference amount.

3. A method as recited in claim 2 wherein comparing and determining whether the bacteria has a drug sensitivity is delayed for a time period which time period initiates upon an initial contact between the bacteria and the antibacterial drug.

4. A method as recited in claim 2 wherein the determining step is conducted on said first and second samples at a time when said first and second samples include a respiration interfering drug.

5. A method as recited in claim 4, wherein said respiration interfering drug is a respiration interfering drug to which bacteria is non-sensitive and to which cell types other than the bacteria located in said samples are sensitive.

6. A method as recited in claim 2 wherein detecting the dissolved oxygen quantity includes detecting a degree oxygen concentration in said test samples based on a total respiration amount outputted by the bacteria in said test samples while lowering the respiration of animal cell types located with the bacteria in the test solution through the use of a respiration interfering drug.

7. A method as recited in claim 2 wherein determining whether the bacteria has a drug sensitivity occurs within 60 minutes of initial contact between said bacteria and antibacterial drug.

8. A method as recited in claim 1 wherein said respiration interfering drug is of a type to which both bacteria and non-bacteria respirating components are sensitive and is in a concentration which results in a greater respiration interference effect in the non-bacteria respirating components of said test sample than in the bacteria respirating components.

9. A method as recited in claim 1, wherein both a respiration interfering drug to which bacteria is sensitive and a respiration interfering drug to which bacteria is not sensitive are used in the first and second samples.

10. A method as recited in claim 1, wherein said respiration interfering drug is of a type to which bacteria is not sensitive.

11. A method as recited in claim 1 further comprising preparing a test solution which includes the bacteria and the liquid medium, and adding an essentially equal quantity of said test solution to first and second culture cells simultaneously with the first culture cell means including the antibacterial drug and the second culture cell being free of any antibacterial drug, and said first and second samples each have a common composition throughout when in said respective first and second cells.

12. A method as recited in claim 11 wherein the test solution originates from a common source and said culture cells are units which are independent and separated from each other.

13. A method as recited in claim 1 wherein the antibacterial drug and bacteria are added in sequence.

14. A method as recited in claim 1 wherein the antibacterial drug and bacteria are added to the liquid simultaneously.

15. An antibacterial drug inspection apparatus, comprising:
at least two culture cells for containing a first and a second test sample, respectively;
first and second oxygen electrode detectors positioned in respective ones of said culture cells for contacting said test samples therein, and said first detector senses a dissolved oxygen quantity in the first test sample and outputs a sensed value for the sensed oxygen quantity, and said second detector senses a dissolved oxygen quantity in the second test sample and outputs a sensed value for the sensed oxygen quantity in the second test sample;
determining means for determining when the sensed value outputted from said first detector in contact with the first test sample containing a liquid medium, a bacteria and an antibacterial drug is essentially different from the sensed value outputted from said second detector in contact with the second test sample containing a same type liquid medium, a same type bacteria and being free of the antibacterial drug such that a determination of whether the bacteria has a drug sensitivity to the antibacterial drug is made when said first and second sensed values are essentially different and wherein said determining means determining when the sensed value outputted from said first detector, while in contact with a test sample containing a liquid medium, a bacteria, a respiration interfering drug, and an antibacterial drug, is essentially different from the sensed value outputted from said second detector while in contact with a test sample containing a same type of liquid medium, a same type of bacteria, a same type of respiration interfering drug and being free of the antibacterial drug.

16. An apparatus as recited in claim 15 further comprising a display section which displays whether or not the bacteria is sensed as having a drug sensitivity to the antibacterial drug.

17. An apparatus as recited in claim 15 further comprising a comparing device for comparing the sensed values outputted and for relaying a comparison result to said determining means, and a control section in communication with said comparing device which delays activation of said comparing device and determining means until a reference period has passed since contact between the bacteria and the antibacterial drug.

18. An apparatus as recited in claim 17 wherein said reference time period is within 60 minutes.

19. An apparatus as recited in claim 15 further comprising a liquid injection device which injects a common liquid solution, which includes the bacteria, simultaneously into the culture cells.

20. An apparatus as recited in claim 15 wherein said cells are separated and independent from each other, and said cells being dimensioned and arranged so as to hold a respective one of said test samples with each test sample having a common composition throughout, and said apparatus further comprising an injection device for injecting said test samples to said cells.

21. An apparatus as recited in claim 15 wherein said determining means determines a total respiration output of all respirating constituents of each of said samples.

22. An antibacterial drug inspection method, comprising:
providing into each of a first and a second container a test sample comprised of a bacteria, a medium, and a respiration interfering drug;
further providing an antibacterial drug to said first container while maintaining the second container free of the antibacterial drug;
detecting a total oxygen quantity of the test sample in said first and second containers with a first and a second oxygen quantity detector respectively placed in said first and second containers with each of the detected oxygen quantities being based on all respiration activity associated with said bacteria while the respirating interfering drug acts to preclude respiration activity of respirating animal cells located in said test samples in addition to the bacteria, and said first and second detectors each outputting a sensed oxygen quantity value;
comparing the outputted sensed values from said detectors with a comparing device which compares the outputted sensed values and produces a comparison result; and determining whether or not the bacteria has a drug sensitivity to said antibacterial drug.

23. An antibacterial drug inspection apparatus, comprising:

- at least two culture cells with two of said cells designed for holding a first and a second test sample, respectively;
- a liquid injection device for providing each of said two culture cells with a liquid component of said test samples;
- a first oxygen electrode detector and a second oxygen electrode detector positioned in respective ones of said culture cells for contact with the test samples therein, and said first detector senses a dissolved oxygen quantity in the first test sample and outputs a sensed value for the sensed oxygen quantity, and said second detector senses a dissolved oxygen quantity in the second test sample and outputs a sensed value for the sensed oxygen quantity in the second test sample;
- determining means for determining when the sensed value outputted from said first detector in contact with the first test sample containing a liquid medium, a bacteria and an antibacterial drug is essentially different from the sensed value outputted from said second detector in contact with the second test sample containing a same type liquid medium, a same type bacteria and being free of the antibacterial drug such that a determination of whether the bacteria has a drug sensitivity to the antibacterial drug is made when said first and second sensed values are essentially different, and wherein said determining means determines a total respiration output of the bacteria in said culture cells while respiration from animal cells in said test samples with the bacteria is precluded due to an inclusion of a respiration interfering drug in said test samples.

\* \* \* \* \*